US00PP30375P2

(12) United States Plant Patent
Egger

(10) Patent No.: US PP30,375 P2
(45) Date of Patent: Apr. 9, 2019

(54) *AGASTACHE* PLANT NAMED 'TNAGAKR'

(50) Latin Name: ***Agastache* hybrid**
Varietal Denomination: TNAGAKR

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,793

(22) Filed: Apr. 25, 2018

(51) Int. Cl.
*A01H 5/02* (2018.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct form of *Agastache* plant characterized by red flowers in large, extended inflorescences, flower color that stays red when planted out in full sun, continuous bloom from spring through fall in Canby, Oreg., excellent branching, a short compact habit, and excellent vigor.

1 Drawing Sheet

Botanical denomination: *Agastache* hybrid.
Variety designation: 'TNAGAKR'.
Trademark designation: Kudos™ Red

BACKGROUND OF THE INVENTION

The present invention relates to a new and distinct cultivar of *Agastache*, given the name, 'TNAGAKR'. *Agastache* is in the family Lamiaceae. This new cultivar is one of several selections of new *Agastache* using hardy and dwarf *Agastache* species in the breeding lines to provide hardiness and compactness. The new cultivar is from a controlled cross using proprietary, unnamed *Agastache* '356-3' as the seed parent and *Agastache* '352-1' as the pollen parent. The new cultivar was selected for its compact habit, hardiness, and bright red flowers.

The trademark designation for the claimed plant is 'Kudos™ Red'.

Compared to the seed parent, *Agastache* '356-3' the new cultivar is taller with larger flowers that stay red in full sun rather than fading to dull red.

Compared to the pollen parent, *Agastache* '352-1' the new cultivar is taller with larger flowers and a better inflorescence.

Compared *Agastache* 'Kudos Coral', U.S. Plant Pat. No. 25,613, the new cultivar has red flowers rather than coral red.

This plant exhibits the following characteristics that make it unique:

1. red flowers in large, extended inflorescences,
2. flower color that stays red when planted out in full sun,
3. continuous bloom from spring through fall in Canby, Oreg.,
4. excellent branching,
5. a short, compact habit, and
6. excellent vigor.

This new cultivar has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescence of *Agastache* 'TNAGAKR' growing outside in the trial field in mid-summer in Canby, Oreg.

FIG. 2 shows a five-month-old *Agastache* 'TNAGAKR' growing in the trial field in mid-summer in Canby, Oreg.

DETAILED PLANT DESCRIPTION

The following is a detailed description of the new *Agastache* cultivar based on observations of nine-month-old specimens in early October growing in full sun in the trail field in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, 5$^{th}$ edition, 2007.

Plant:

*Form*.—Upright.
*Type*.—Herbaceous perennial.
*Cold hardiness*.—USDA Zone 6-10.
*Size*.—Grows to 66 cm wide and 53 cm tall to the top of the flowers.
*Vigor*.—Excellent.

*Branching*.—About 10 main stems from the base, these branch at every node.

*Stem*.—Square in cross section, grows to 7 mm wide and 22 cm tall to the first flower, pubescent, internodes range from 2.4 cm to 7.2 cm long, Yellow-Green 146A.

*Roots*.—White 155B, fibrous, plants root easily from stem tip cuttings.

Leaf:

*Type*.—Simple.

*Arrangement*.—Opposite.

*Shape*.—Ovate.

*Venation*.—Pinnate.

*Margins*.—Coarsely serrate.

*Apex*.—Acute to obtuse.

*Base*.—Cuneate to auriculate.

*Blade size*.—Grows to 56 mm long and 33 mm wide.

*Surface texture*.—Pubescent on both sides.

*Petiole description*.—Grows to 23 mm long and 4 mm wide, pubescent, Yellow-Green 147B.

*Leaf color*.—Top side Yellow-Green 147A with veins Yellow-Green 147B, bottom side closest to Greyed-Green 191A with veins Greyed-Green 191B.

*Fragrance*.—Aromatic.

Inflorescence:

*Type*.—Terminal spike.

*Number of flowers*.—Up to 500 per spike.

*Size of inflorescence*.—Grows to 18 cm tall and 5.5 cm wide.

*Rachis*.—Grows to 38 mm tall and 25 mm wide, pubescent, Yellow-Green 146B.

*Pedicel*.—Grows to 2 mm long, pubescent, Yellow-Green 146D.

*Bloom period*.—June through frost in Canby, Oreg.

Flower bud:

*Size*.—17 mm long and 5 mm wide at the widest point prior to opening.

*Description*.—Tubular.

*Surface texture*.—Pubescent.

*Color*.—Red 46B.

Flower:

*Type*.—Zygomorphic.

*Shape*.—Bilabiate, tubular.

*Size*.—21 mm long and 6 mm wide.

*Corolla description*.—Grow to 18 mm long and spreads to 6 mm wide; both sides Red 47B; tube 8 mm long and 1 mm to 4 mm wide, pubescent inside and outside; five lobes, upper lobe, 3 mm long and 4.5 mm wide, reflexed, tip rectangular, margin entire; 4 lower lobes, two spreading sideways and curl back, each 3.5 mm long and 1.5 mm wide, tips obtuse to acute, margin entire; two bottom lobes, reflexed, each 4 mm long and 2.5 mm deep.

*Calyx description*.—Campanulate, 5.4 mm long and 3.2 mm wide, pubescent outside and glabrous inside, 5 lobed, lobes ovate, 1.5 mm long, entire, acute, when young Yellow-Green 144B becoming Greyed-Orange 176B.

*Pistil description*.—24 mm long, ovary 1 mm long, Yellow-Green 145D, style 22 mm long, bottom half White NN155B darkening on top half to Red 46C, stigma two-parted, 1 mm deep, Red 46C.

*Stamen description*.—4 in number, paired and recessed, top two 8 mm long and bottom two 5 mm long, filaments Red 48D, anthers 0.5 mm long Greyed-Orange 177C, pollen moderate, White NN155A.

*Fragrance*.—Aromatic.

*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described herein.

* * * * *

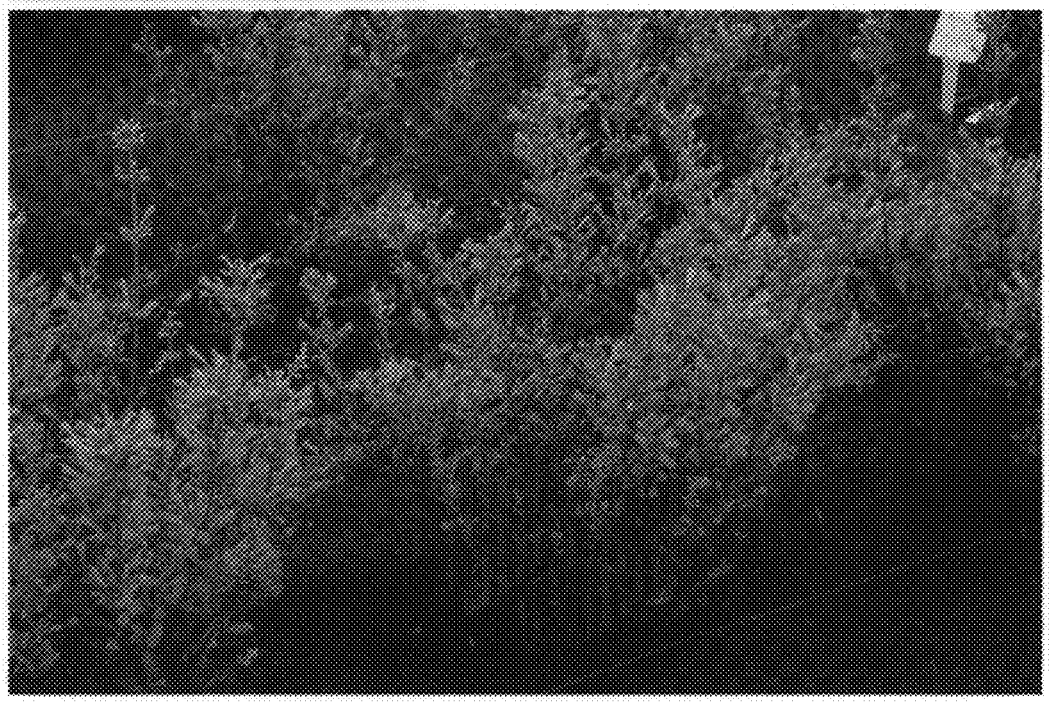

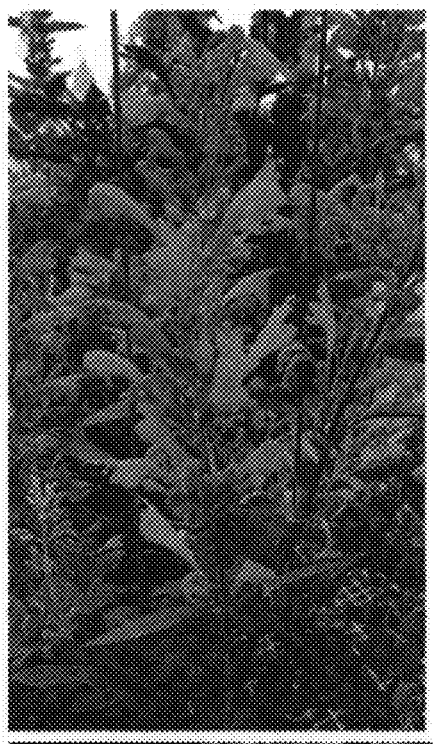
FIG. 1 Left
FIG. 2 Below